United States Patent
Kaku

(10) Patent No.: US 10,674,892 B2
(45) Date of Patent: Jun. 9, 2020

(54) IMAGE PROCESSOR, IMAGE PROCESSING METHOD, AND ENDOSCOPE SYSTEM

(71) Applicant: FUJIFILM Corporation, Tokyo (JP)

(72) Inventor: Toshihiko Kaku, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 298 days.

(21) Appl. No.: 15/605,913

(22) Filed: May 25, 2017

(65) Prior Publication Data

US 2017/0258296 A1 Sep. 14, 2017

Related U.S. Application Data

(63) Continuation of application No. PCT/JP2016/052323, filed on Jan. 27, 2016.

(30) Foreign Application Priority Data

Jan. 29, 2015 (JP) .................................. 2015-015179
Aug. 25, 2015 (JP) .................................. 2015-166101

(51) Int. Cl.
*A61B 1/00* (2006.01)
*G02B 23/24* (2006.01)
(Continued)

(52) U.S. Cl.
CPC ........ *A61B 1/00009* (2013.01); *A61B 1/0005* (2013.01); *A61B 1/04* (2013.01);
(Continued)

(58) Field of Classification Search
CPC . A61B 1/00009; A61B 1/0005; A61B 5/0084; A61B 1/3137; A61B 5/1032;
(Continued)

(56) References Cited

U.S. PATENT DOCUMENTS

| | | |
|---|---|---|
| 7,647,092 B2 | 1/2010 | Motz et al. |
| 2005/0059894 A1 | 3/2005 | Zeng et al. |

(Continued)

FOREIGN PATENT DOCUMENTS

| | | |
|---|---|---|
| EP | 1704816 | 9/2006 |
| EP | 3005933 | 4/2016 |

(Continued)

OTHER PUBLICATIONS

"Office Action of Japan Counterpart Application," dated Oct. 6, 2017,with English translation thereof, p. 1-p. 6, in which the listed references were cited.

(Continued)

*Primary Examiner* — Eric F Winakur
*Assistant Examiner* — Abid A Mustansir
(74) *Attorney, Agent, or Firm* — JCIPRNET

(57) ABSTRACT

An image processor calculates diagnosis support parameters on the basis of the state of blood vessels of an observation object. The image processor includes an image acquisition unit that acquires an endoscopic image, a blood vessel extraction unit that extracts blood vessels, using the endoscopic image, a blood vessel information calculation unit, and a blood vessel parameter calculation unit. The blood vessel information calculation unit calculates a plurality of items of blood vessel information including at least two or more among the number of pieces, the number of branches, a branch angle, a distance between branch points, the number of intersections, thickness, a change in thickness, the degree of complexity of a change in thickness, length, intervals, depth with a mucous membrane as a reference, and the like. The blood vessel parameter calculation unit calculates blood vessel parameters by calculating using the plurality of items of blood vessel information.

10 Claims, 10 Drawing Sheets

(51) Int. Cl.
| | |
|---|---|
| *A61B 5/00* | (2006.01) |
| *H04N 7/18* | (2006.01) |
| *G06T 7/00* | (2017.01) |
| *A61B 1/04* | (2006.01) |
| *A61B 1/313* | (2006.01) |
| *A61B 5/02* | (2006.01) |
| *A61B 5/026* | (2006.01) |
| *A61B 5/103* | (2006.01) |
| *A61B 5/1455* | (2006.01) |
| *A61B 5/1459* | (2006.01) |

(52) U.S. Cl.
CPC .......... *A61B 1/3137* (2013.01); *A61B 5/0084* (2013.01); *A61B 5/02007* (2013.01); *A61B 5/0261* (2013.01); *A61B 5/1032* (2013.01); *A61B 5/1459* (2013.01); *A61B 5/14551* (2013.01); *A61B 5/489* (2013.01); *A61B 5/7278* (2013.01); *A61B 5/7282* (2013.01); *G02B 23/24* (2013.01); *G06T 7/0012* (2013.01); *H04N 7/18* (2013.01); *A61B 1/041* (2013.01); *A61B 5/0073* (2013.01); *A61B 2576/02* (2013.01); *G06T 2207/10024* (2013.01); *G06T 2207/10068* (2013.01); *G06T 2207/30101* (2013.01)

(58) Field of Classification Search
CPC . A61B 5/02007; A61B 5/0261; A61B 5/7282; A61B 5/14551; A61B 5/1459; A61B 5/489; A61B 5/7278; A61B 1/04; A61B 1/041; A61B 2576/02; A61B 5/0073; G06T 7/0012; G06T 2207/30101; G06T 2207/10068; G06T 2207/10024; H04N 7/18; G02B 23/24
See application file for complete search history.

(56) References Cited

U.S. PATENT DOCUMENTS

| | | | |
|---|---|---|---|
| 2011/0245642 A1 | 10/2011 | Minetoma | |
| 2012/0154567 A1* | 6/2012 | Yamaguchi | A61B 1/0638 348/68 |
| 2012/0190922 A1* | 7/2012 | Kaku | A61B 1/00009 600/109 |
| 2012/0253157 A1* | 10/2012 | Yamaguchi | A61B 1/0638 600/328 |
| 2012/0302847 A1* | 11/2012 | Ozawa | A61B 1/00009 600/339 |
| 2015/0181185 A1 | 6/2015 | Ikemoto et al. | |
| 2015/0282694 A1* | 10/2015 | Morimoto | A61B 1/0005 600/339 |
| 2016/0120449 A1 | 5/2016 | Chiba | |

FOREIGN PATENT DOCUMENTS

| | | |
|---|---|---|
| EP | 3251581 | 12/2017 |
| JP | 2004024656 | 1/2004 |
| JP | 2007505645 | 3/2007 |
| JP | 2009-207541 | 9/2009 |
| JP | 4493637 | 6/2010 |
| JP | 2010172673 | 8/2010 |
| JP | 2010249835 | 11/2010 |
| JP | 2014018333 | 2/2014 |
| JP | 2014230647 | 12/2014 |
| JP | 2015012582 | 1/2015 |
| WO | 2013132400 | 9/2013 |
| WO | 2014114814 | 7/2014 |
| WO | 2014192781 | 12/2014 |
| WO | 2014200065 | 12/2014 |

OTHER PUBLICATIONS

"Search Report of Europe Counterpart Application", dated Jan. 22, 2018, p. 1-p. 39, in which the listed references were cited.

"Office Action of Japan Counterpart Application," with English translation thereof, dated Dec. 26, 2017, p. 1-p. 6, in which the listed reference was cited.

Office Action of Japan Counterpart Application, with English translation thereof, dated Mar. 6, 2018, pp. 1-6.

"Office Action of Europe Counterpart Application," dated Aug. 21, 2019, p. 1-p. 6.

* cited by examiner

IMAGE PROCESSOR, IMAGE PROCESSING METHOD, AND ENDOSCOPE SYSTEM

CROSS-REFERENCE TO RELATED APPLICATION

This application is a Continuation of PCT International Application PCT/JP2016/052323 filed on 27 Jan. 2016, which claims priority under 35 USC 119(a) from Japanese Patent Application No. 2015-015179 filed on 29 Jan. 2015, and Japanese Patent Application No. 2015-166101 filed on 25 Aug. 2015. The above application is hereby expressly incorporated by reference, in its entirety, into the present application.

BACKGROUND OF THE INVENTION

1. Field of the Invention

The present invention relates to an image processor, an image processing method, and an endoscope system that calculates data, such as numerical values provided for diagnosis using an endoscopic image, using the endoscopic image captured by an endoscope.

2. Description of the Related Art

In the medical field, diagnosis using endoscope systems including a light source device, an endoscope, and a processor device has been performed widely. In the diagnosis using the endoscope systems, an insertion part of the endoscope is inserted into a subject, illumination light is radiated from a distal end part, and an observation object (such as a mucous membrane within the subject) irradiated with the illumination light is imaged by an imaging sensor loaded on the distal end part of the endoscope. An image of the observation object is generated using image signals obtained by the imaging, and is displayed on a monitor.

In the endoscope systems, generally, an image (hereinafter referred to as an observation image) in which the observation object is observable in natural tone is displayed by radiating white illumination light (also referred to as normal light) to image the observation object. Moreover, endoscope systems that obtain an image (hereinafter referred to as a special observation image) in which blood vessels, pit patterns, and the like of the observation object are enhanced by using light having a specific wavelength band as the illumination light have also spread. Since information on the blood vessels, the pit patterns, and the like are important diagnosis material, the special observation image in which these are enhanced is particularly useful for diagnosis.

Additionally, in recent years, endoscope systems or diagnosis support devices that support doctors' diagnosis by calculating the depth, thickness, and density of blood vessels, and diagnosis indexes obtained from color balance of pixels representing the blood vessels, using the endoscopic image (the normal observation image, the special observation image, or image signals for generating these) captured by the endoscope are also known (JP4493637B and JP5395725B (corresponding to U.S. Pat. Pub. No. 2011/245,642)).

Information on blood vessels (hereinafter referred to as blood vessel information) that can be calculated using the endoscopic image as in JP4493637B and JP5395725B is information useful for diagnosis as described above. However, doctors do not perform diagnosis on the basis of one kind of blood vessel information out of the blood vessel information, such as the depth, thickness, and density of the blood vessels, and the diagnosis indexes obtained from the color balance of pixels representing the blood vessels, but complexly perform diagnosis in consideration of a plurality of items of blood vessel information, including blood vessel information that is not evaluated by related-art endoscope systems other than the above blood vessel information. For example, the thickness of the blood vessels and the density of the blood vessels are respectively blood vessel information useful for diagnosis. However, the state of the observation object is not necessarily differentiated only by the thickness of the blood vessels being a specific thickness, or the density of the blood vessel being a specific density. Diagnoses is performed from multifaceted and complex points of sight by taking into consideration a plurality of items of blood vessel information that the state of the observation object is a specific lesion because the thickness of the blood vessels is equal to or greater than the specific thickness and the density of the blood vessels is equal to or greater than beyond the specific value.

In accordance with the actual conditions of the multifaceted and complex diagnosis as described above, in recent years, it is required that endoscope systems or image processors for analyzing an endoscopic image calculate information or the like that is more direct and useful than the blood vessel information calculated in JP4493637B and JP5395725B, and support doctors' diagnosis.

SUMMARY OF THE INVENTION

An object of the invention is to provide an image processor, an image processing method, and an endoscope system that uses a plurality of items of blood vessel information, and calculates diagnosis support parameters (hereinafter referred to as blood vessel parameters) based on the state of blood vessels of an observation object, in accordance with actual conditions of diagnosis using an endoscopic image.

An image processor of the invention includes an image acquisition unit, a blood vessel extraction unit, a blood vessel information calculation unit, and a blood vessel parameter calculation unit. The image acquisition unit acquires an endoscopic image captured by the endoscope. The blood vessel extraction unit extracts blood vessels from the observation object projected on the endoscopic image, using the endoscopic image. The blood vessel information calculation unit calculates a plurality of items of blood vessel information including at least two or more among the number, the number of branches, a branch angle, a distance between branch points, the number of intersections, thickness, a change in thickness, the degree of complexity of a change in thickness, length, spacing, depth with the mucous membrane as a reference, a height difference, inclination, area, density, contrast, color, a change in color, the degree of meandering, blood concentration, the degree of oxygen saturation, the percentage of arteries, the percentage of veins, the concentration of an administered pigment, a traveling pattern, and a blood flow rate, in terms of blood vessels. The blood vessel parameter calculation unit calculates a blood vessel parameter by calculating using the plurality of items of blood vessel information.

It is preferable that the blood vessel information is the amount of statistics in a whole or partial region of the endoscopic image.

It is preferable that the blood vessel information is a maximum value, a minimum value, an average value, or a median value in the whole or partial region of the endoscopic image.

It is preferable that the blood vessel parameter calculation unit performs calculating by performing weighting on the plurality of items of blood vessel information, and calculates the blood vessel parameter.

It is preferable that the blood vessel parameter calculation unit performs the weighting, using predetermined coefficients through machine learning.

It is preferable to further include a determination unit that determines a state of the mucous membrane of the observation object, using the blood vessel parameter.

It is preferable that the determination unit determines the state of the mucous membrane of the observation object as any one of three or more kinds of states including normality, adenoma, and cancer, using the blood vessel parameter.

It is preferable that the determination unit determines the state of the mucous membrane of the observation object as any one of states including normality, hyperplastic polyp, SSA/P, adenoma, laterally spreading tumor, and cancer, using the blood vessel parameter.

It is preferable that the determination unit further determines the stage of cancer, using the blood vessel parameter, in a case where the state of the mucous membrane of the observation object is cancer.

An endoscope system of the invention includes an endoscope that images an observation object; and a processor device. The processor device has an image acquisition unit, a blood vessel extraction unit, a blood vessel information calculation unit, and a blood vessel parameter calculation unit. The image acquisition unit acquires an endoscopic image captured by the endoscope. The blood vessel extraction unit extracts blood vessels of the observation object projected on the endoscopic image, using the endoscopic image. The blood vessel information calculation unit calculates a plurality of items of blood vessel information including at least two or more among the number, the number of branches, a branch angle, a distance between branch points, the number of intersections, thickness, a change in thickness, the degree of complexity of a change in thickness, length, spacing, depth with the mucous membrane as a reference, a height difference, inclination, area, density, contrast, color, a change in color, the degree of meandering, blood concentration, the degree of oxygen saturation, the percentage of arteries, the percentage of veins, the concentration of an administered pigment, a traveling pattern, and a blood flow rate, in terms of blood vessels. The blood vessel parameter calculation unit calculates a blood vessel parameter by calculating using the plurality of items of blood vessel information.

An image processing method of the invention includes a step in which an image acquisition unit acquires an endoscopic image captured by an endoscope; a step in which a blood vessel extraction unit extracts blood vessels from an observation object projected on the endoscopic image, using the endoscopic image; a step in which a blood vessel information calculation unit calculates a plurality of items of blood vessel information including at least two or more among the number of pieces, the number of branches, a branch angle, a distance between branch points, the number of intersections, thickness, a change in thickness, the degree of complexity of a change in thickness, length, intervals, depth with a mucous membrane as a reference, a height difference, inclination, area, density, contrast, color, a change in color, the degree of meandering, blood concentration, the degree of oxygen saturation, the percentage of arteries, the percentage of veins, the concentration of an administered pigment, a traveling pattern, and a blood flow rate, in terms of the blood vessels; and a step in which a blood vessel parameter calculation unit calculates a blood vessel parameter by performing calculation using the plurality of items of blood vessel information.

Since the image processor, the image processing method, and the endoscope system of the invention calculate the plurality of items of blood vessel information, using the endoscopic image, and calculate the blood vessel parameters, using the plurality of items of calculated blood vessel information in accordance with actual conditions of diagnosis using the endoscopic image, doctors' diagnosis can be supported more directly than in the related art.

DESCRIPTION OF THE PREFERRED EMBODIMENTS

Figure 1:
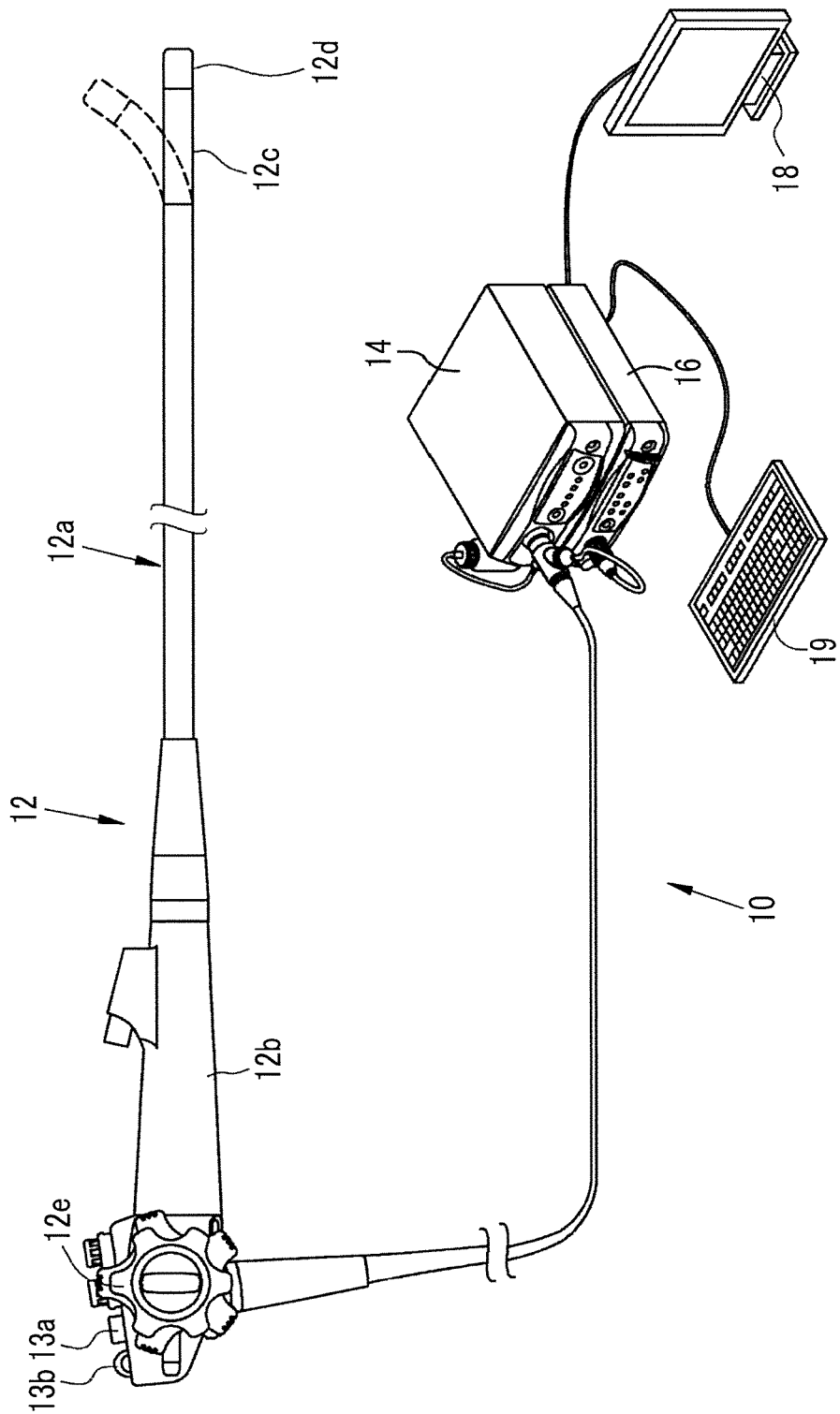
FIG. 1 is an external view of an endoscope system.

As illustrated in FIG. 1, an endoscope system 10 has an endoscope 12, a light source device 14, a processor device 16, a monitor 18, and a console 19. The endoscope 12 is optically connected to the light source device 14, and is electrically connected to the processor device 16. The endoscope 12 has an insertion part 12a to be inserted into a subject, an operating part 12b provided at a base end portion of the insertion part 12a, and a bending part 12c and a distal end part 12d provided on a distal end side of the insertion part 12a. By operating an angle knob 12e of the operating part 12b, the bending part 12c makes a bending motion. The distal end part 12d is directed in a desired direction by this bending motion.

Additionally, the operating part 12b is provided with a still image acquisition instruction part 13a and a zooming operation part 13b other than the angle knob 12e. The still image acquisition instruction part 13a is used in order to input a still image acquisition instruction to the endoscope system 10. As the still image acquisition instruction, there are a freeze instruction for displaying a still image of an observation object on the monitor 18 and a release instruction for saving the still image in a storage. The zooming operation part 13b is used in order to input an imaging magnification change instruction for changing imaging magnification.

The processor device 16 is electrically connected to the monitor 18 and the console 19. The monitor 18 outputs and displays the image of the observation object, information accompanying the image, and the like. The console 19 functions as a user interface that receives input operation, such as function setting.

Figure 2:
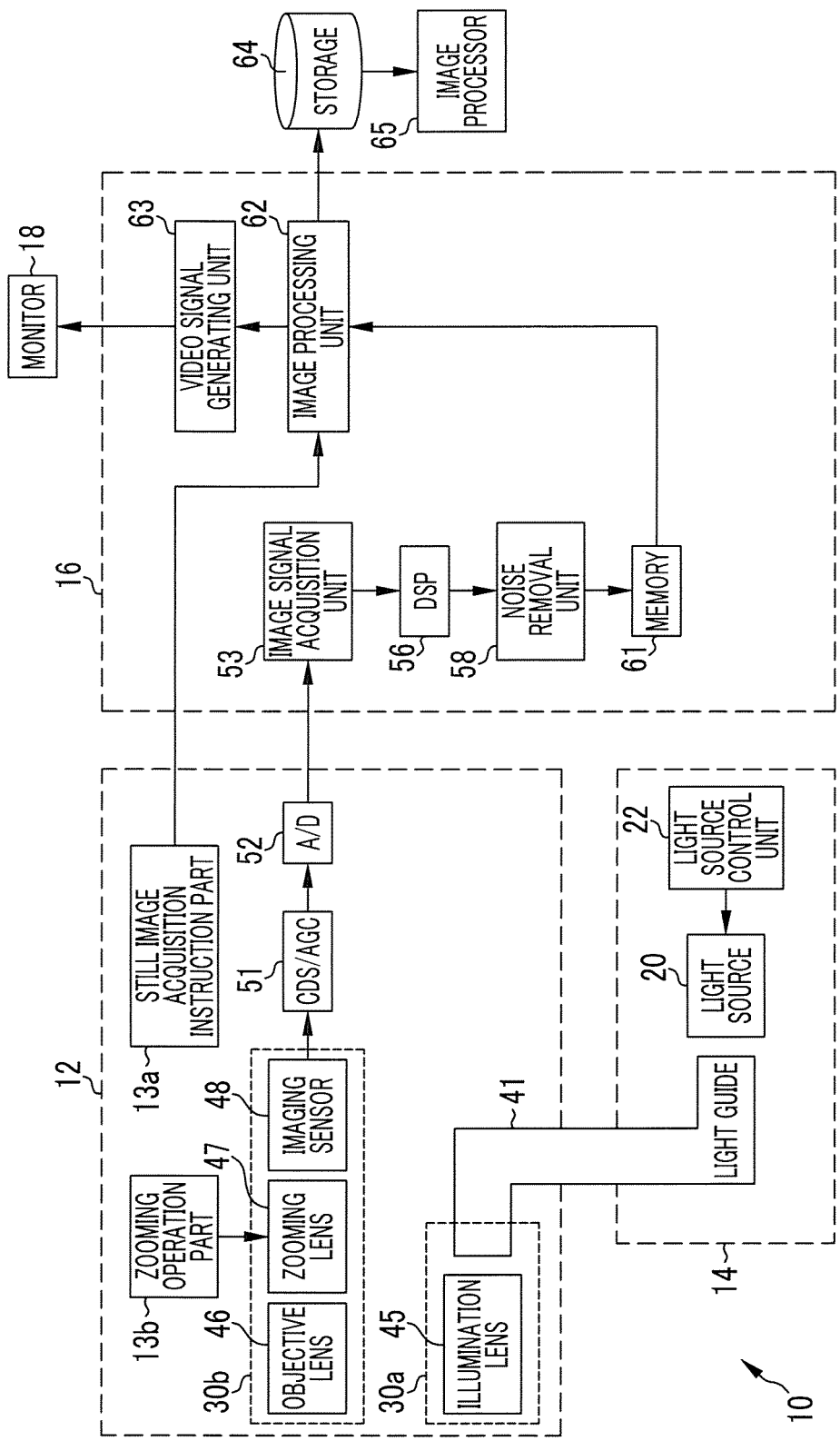
FIG. 2 is a block diagram illustrating the functions of the endoscope system.

As illustrated in FIG. 2, the light source device 14 includes a light source 20 that emits illumination light to be radiated to the observation object, and a light source control unit 22 that controls the light source 20. The light source 20 is constituted by, for example, semiconductor light sources, such as light emitting diodes (LED) in a plurality of colors, a combination of a laser diode and a fluorescent material, or a halogen light source, such as a xenon lamp. Additionally, optical filters for adjusting the wavelength bands of light beams emitted from the LEDs are included in the light source 20. The light source control unit 22 controls the quantity of light of the illumination light by ON and OFF of the LEDs and the adjustment of the driving currents and driving voltages of the LEDs. Additionally, the light source control unit 22 controls the wavelength band of the illumination light by changes of the optical filters.

The endoscope system 10 has two types of observation modes including a normal observation mode for observing the observation object with a normal observation image, and a special observation mode for observing the observation object with a special observation image. In a case where an observation mode is the normal observation mode, the light source control unit 22 generates substantially white illumination light with the light source 20. In a case where an observation mode is the special observation mode, the light source control unit 22 generates illumination light (hereinafter referred to as narrow-band light) having a specific narrow wavelength band with the light source 20. The observation modes are switched by a mode changeover switch (not illustrated) provided in the operating part 12b.

The illumination light emitted from the light source 20 enters a light guide 41 inserted into the insertion part 12a. The light guide 41 is built in the endoscope 12 and a universal cord, and propagates the illumination light up to the distal end part 12d of the endoscope 12. The universal cord is a cord that connects the endoscope 12, and the light source device 14 and the processor device 16 together. In addition, a multimode fiber can be used as the light guide 41. As an example, a fine-diameter fiber cable of which the core diameter is 105 μm, the clad diameter is 125 μm, and a diameter including a protective layer used as an outer cover is φ0.3 mm to 0.5 mm can be used.

The distal end part 12d of the endoscope 12 is provided with an illumination optical system 30a and an imaging optical system 30b. The illumination optical system 30a has an illumination lens 45, and the illumination light propagated by the light guide 41 is radiated to the observation object via the illumination lens 45. The imaging optical system 30b has an objective lens 46, a zoom lens 47, and an imaging sensor 48. Various kinds of light, such as reflected light, scattered light, and fluorescence from the observation object, enters the imaging sensor 48 via the objective lens 46 and the zoom lens 47. Accordingly, the image of the observation object is formed on the imaging sensor 48. The zoom lens 47 is movable between a tele-end and a wide end by operating the zooming operation part 13b, and magnifies or reduces the observation object of which the image is to be formed on the imaging sensor 48.

The imaging sensor 48 is a color imaging sensor in which any one of color filters in R (red), G (green), or B (blue) is provided for each pixel, and image signals of respective RGB colors are output by imaging the observation object. As the imaging sensor 48, a charge coupled device (CCD) imaging sensor or a complementary metal-oxide semiconductor (CMOS) imaging sensor is available. Additionally, instead of the imaging sensor 48 provided with color filters in original colors, a complementary color imaging sensor including complementary color filters in C (cyan), M (magenta), Y (yellow), and G (green) may be used. In a case where the complementary color imaging sensor is used, image signals of four colors of CMYG are output. For this reason, the same RGB image signals as those in the imaging sensor 48 can be obtained by converting the image signals of four colors of CMYG into image signals of three colors of RGB through color conversion between complementary colors and original colors. Additionally, instead of the imaging sensor 48, a monochrome sensor that is not provided with the color filters may be used.

The image signals output from the imaging sensor 48 are transmitted to a CDS/AGC circuit 51. The CDS/AGC circuit 51 performs correlated double sampling (CDS) and automatic gain control (AGC) on the image signals that are analog signals. The image signals that have passed through the CDS/AGC circuit 51 are converted into digital image signals by an analog-to-Digital (A/D) converter 52. The digital image signals after the A/D conversion are input to the processor device 16.

The processor device 16 includes an image signal acquisition unit 53, a digital signal processor (DSP) 56, a noise removal unit 58, a memory 61, a signal processing unit 62, and a video signal generating unit 63.

The image signal acquisition unit 53 acquires the digital image signals from the endoscope 12. The DSP 56 performs various kinds of signal processing, such as defect correction processing, offset processing, gain correction processing, linear matrix processing, gamma conversion processing, demosaic processing, and the like, on the image signals acquired by the image signal acquisition unit 53. In the defect correction processing, a signal of a defective pixel of the imaging sensor 48 is corrected. In the offset processing, a dark current component is removed from an image signal subjected to the defect correction processing, and an accurate zero level is set. In the gain correction processing, a signal level is adjusted by multiplying the image signal after the offset processing by a specific gain.

The linear matrix processing for enhancing color reproducibility is performed on the image signal after the gain correction processing. Then, brightness and saturation are adjusted by the gamma conversion processing. The demosaic processing (also referred to as equalization processing of a grade or synchronization processing) is performed on the image signal after the gamma conversion processing, and a signal of a color that runs short in each pixel is generated by interpolation. Using this demosaic processing, all pixels have signals of respective RGB colors. The noise removal unit 58 performs noise removal processing using, for example, a moving average method, a median filter method, or the like on the image signal subjected to the demosaic processing or the like by the DSP 56, and removes noise. The image signal from which noise is removed is stored in the memory 61.

The signal processing unit 62 acquires the image signal after the noise removal from the memory 61. Signal processing, such as color conversion processing, color enhancement processing, and structure enhancement processing, is performed on the acquired image signal, as the need arises, and an endoscopic image in color on which the observation object is projected is generated. The color conversion processing is the processing of performing conversion of a color on the image signal through 3×3 matrix processing, gradation conversion processing, three-dimensional look-up table (LUT) processing, and the like. The color enhancement processing is performed on the image signal subjected to the color conversion processing. The structure enhancement processing is, for example, the processing of enhancing specific tissue and structure included in the observation object, such as blood vessels and pit patterns, and is performed on the image signal after the color enhancement processing. Since the endoscopic image generated by the signal processing unit 62 is the normal observation image in a case where an observation mode is the normal observation mode and is the special observation image in a case where an observation mode is the special observation mode, the contents of the color conversion processing, the color enhancement processing, and the structure enhancement processing differ depending on the observation modes. In the case of the normal observation mode, the signal processing unit 62 performs the above various kinds of signal processing in which the observation object has a natural tone, and generates the normal observation image. In the case of the special observation mode, the signal processing unit 62 performs the above various kinds of signal processing of enhancing at least the blood vessels of the observation object, and generates the special observation image. In the special observation image generated by the signal processing unit 62, a blood vessel (a so-called surface layer blood vessel) at a relatively shallow position within the observation object with the surface of a mucous membrane as a reference has a magenta-based color (for example, brown), and a blood vessel (a so-called middle-depth-layer blood vessel) at a relatively deep position within the observation object with the surface of the mucous membrane as the reference has a cyan-based color (for example, green). For this reason, the blood vessels of the observation object are enhanced with differences in color with respect to the mucous membrane expressed by a pink-based color.

The endoscopic image generated by the signal processing unit 62 is input to the video signal generating unit 63. The video signal generating unit 63 converts the input endoscopic image into video signals for being output to and displayed on the monitor 18. Additionally, assuming that the release instruction is input by the operation of the still image acquisition instruction part 13a, the signal processing unit 62 saves the generated endoscopic image in a storage 64. The storage 64 is an external storage in which a local area network (LAN) or the like is connected to the processor device 16, and is, for example, a file server of a system that files the endoscopic image, such as a picture archiving and communication system (PACS), a network attached storage (NAS), or the like. The endoscopic image saved in the storage 64 is used in an image processor 65.

Figure 3:
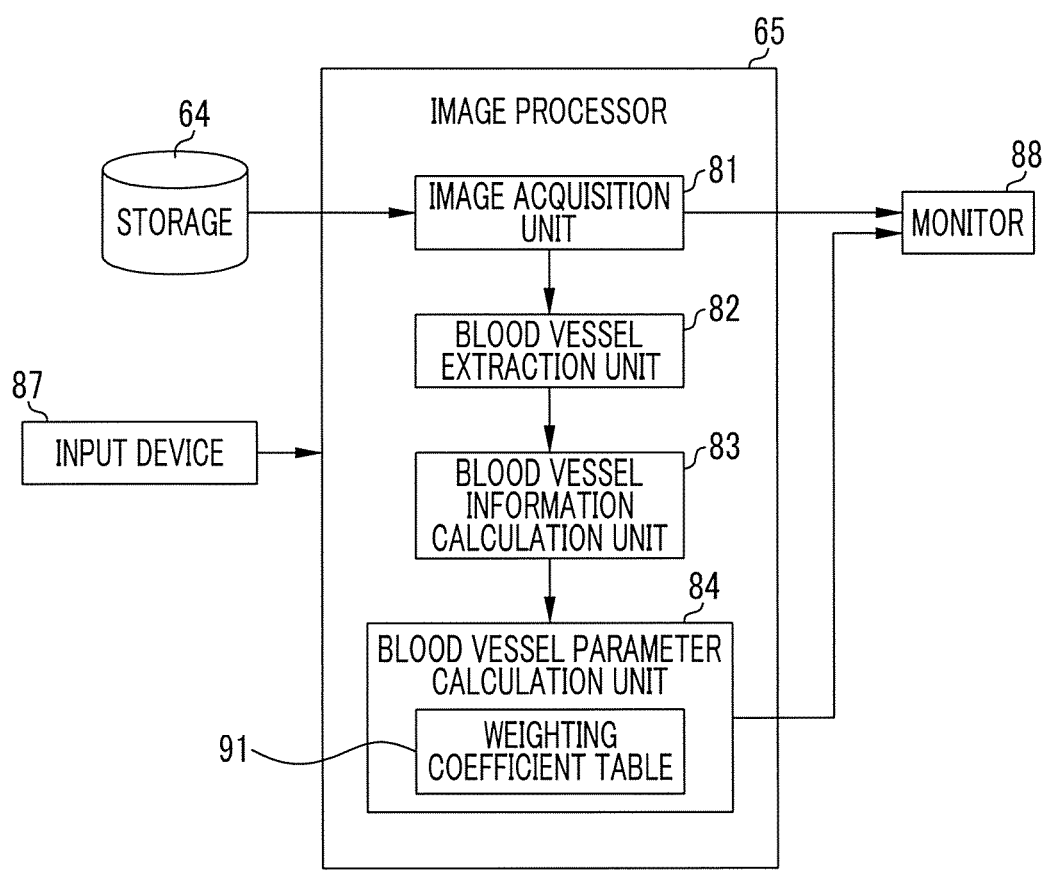
FIG. 3 is a block diagram illustrating the functions of an image processor.

The image processor 65 is a device that performs image processing on the endoscopic image and calculates blood vessel parameters for diagnosis support. As illustrated in FIG. 3, the image processor 65 includes an image acquisition unit 81, a blood vessel extraction unit 82, a blood vessel information calculation unit 83, and a blood vessel parameter calculation unit 84. Additionally, an input device 87 including a pointing device, a keyboard, and the like to be used for pointing or the like of a region of interest (ROI), and a monitor 88 for displaying the endoscopic image, the blood vessel parameters, and the like are connected to the image processor 65.

The image acquisition unit 81 acquires the endoscopic image captured by the endoscope 12 from the storage 64. Although there are the normal observation image and the special observation image as the endoscopic image saved in the storage 64, in the present embodiment, the image acquisition unit 81 acquires the special observation image, in which the blood vessel is enhanced, from the storage 64.

The blood vessel extraction unit 82 extracts the blood vessels from the observation object projected on the endoscopic image, using the endoscopic image acquired by the image acquisition unit 81. The blood vessel extraction unit 82 extracts the blood vessels from the endoscopic image, for example, with a frequency filter or the like. In the present embodiment, the blood vessel extraction unit 82 extracts the blood vessels from the overall endoscopic image acquired by the image acquisition unit 81. However, in a case where an area of interest is specified, the blood vessels may be extracted only within the specified area of interest.

The blood vessel information calculation unit 83 calculates a plurality of items of blood vessel information including at least two or more among the number, the number of branches, a branch angle, a distance between branch points, the number of intersections, thickness, a change in thickness, the degree of complexity of a change in thickness, length, spacing, depth with the mucous membrane as a reference, a height difference, inclination, area, density, contrast, color, a change in color, the degree of meandering, blood concentration, the degree of oxygen saturation, the percentage of arteries, the percentage of veins, the concentration of an administered pigment, a traveling pattern, or a blood flow rate, in terms of blood vessels. In the present embodiment, the blood vessel information calculation unit 83 calculates all the above blood vessel information as much as possible.

The number of blood vessels is the number of blood vessels extracted within the overall endoscopic image or the area of interest. The number of the blood vessels is calculated, for example, using the number of branch points of the extracted blood vessels (the number of branches), the number of intersection points with other blood vessels (the number of intersections), or the like. The branch angle of the blood vessels is an angle that two blood vessels forms at a branch point. The distance between the branch points is a linear distance between an arbitrary branch point and its adjacent branch point, or a length along a blood vessel from the arbitrary branch point and its adjacent branch point.

The number of intersections of the blood vessels is the number of intersection points where blood vessels with different depths under the mucous membrane intersect each other on the endoscopic image. More specifically, the number of intersections of the blood vessels is the number of times with which a blood vessel at a relatively shallow position under the mucous membrane crosses a blood vessel at a relatively deep position.

The thickness (vessel diameter) of the blood vessels is a distance between the blood vessel and a boundary line of the mucous membrane, and is counted, for example, by counting the number of pixels along the lateral direction of a blood vessel through the blood vessel from an edge of the extracted blood vessel. Hence, the thickness of the blood vessels is the number of pixels. However, in a case where an object distance, a zoom magnification, and the like in the event that the endoscopic image is captured are known, the thickness can be converted into the unit of length, such as "µm" as the need arises.

The change in the thickness of the blood vessels is blood vessel information on variations in the thickness of the blood vessel, and is also referred to as the degree of aperture inequality. The change in the thickness of the blood vessels is, for example, the change rate (also referred to as the degree of dilation) of the vessel diameter. The change rate of the vessel diameter is obtained by "Change rate (%) of vessel diameter=Minimum diameter/Maximum diameter× 100", using the thickness (minimum diameter) of a thinnest portion of a blood vessel, and the thickness (maximum diameter) of a thickest portion of the blood vessel.

In addition, in a case where an endoscopic image obtained by imaging the observation object in the past inspection and an endoscopic image obtained by imaging the same observation object in subsequent new inspection are used, a time change in the thickness of the blood vessel extracted from the endoscopic image obtained in the subsequent new inspection with respect to the thickness of the same blood vessel extracted from the endoscopic image obtained in the past inspection may be used as the change in the thickness of the blood vessels.

Additionally, the percentage of a smaller-diameter part or the percentage of a larger-diameter part may be calculated as the change in the thickness of the blood vessels. The smaller-diameter part is a portion of which the thickness is equal to or smaller than a threshold value and the larger-diameter part is a portion of which the thickness is larger than the threshold value. The percentage of the smaller-diameter part is obtained by "Percentage (%) of smaller-diameter part=Length of smaller-diameter part/Length of blood vessel×100" Similarly, the percentage of the larger-diameter part is obtained by "Percentage (%) of larger-diameter part=Length of larger-diameter part/Length of blood vessel×100".

The degree of complexity of the change in the thickness of the blood vessels (hereinafter referred to as "the degree of complexity of a thickness change") is blood vessel information showing how complicated the change is in a case where the thickness of the blood vessels changes, and is blood vessel information calculated by combining a plurality of items of blood vessel information (that is, the change rate of the vessel diameter, the percentage of the smaller-diameter part, or the percentage of the larger-diameter part) showing the change in the thickness of the blood vessel. The degree of complexity of the thickness change can be obtained, for example, by the product of the change rate of the vessel diameter and the percentage of the smaller-diameter part.

The length of the blood vessels is the number of pixels counted in a longitudinal direction of an extracted blood vessel.

The spacing of the blood vessels is the number of pixels representing the mucous membrane between edges of extracted blood vessels. In a case where there is one extracted blood vessel, the spacing between blood vessels does not have a value.

The depth of the blood vessels is measured on the basis of the mucous membrane (specifically, the surface of the mucous membrane). The depth of the blood vessels with this mucous membrane as a reference can be calculated, for example, on the basis of the color of a blood vessel. In the case of the special observation image, a blood vessel at a position near the surface of the mucous membrane is expressed in the magenta-based color and a blood vessel at a position distant from the surface of the mucous membrane and deep under the mucous membrane is expressed in the cyan-based color. Thus, the blood vessel information calculation unit 83 calculates the depth of the blood vessels with the mucous membrane as a reference for each pixel, on the basis of the balance between signals in respective colors of R, G, and B of pixels extracted as the blood vessels.

The height difference of the blood vessels is the magnitude of a difference in the depth of a blood vessel. For example, the height difference of one blood vessel to be observed is obtained from a difference between the depth (the maximum depth) of a deepest place of this blood vessel, and the depth (minimum depth) of a shallowest place. The height difference is zero in a case where the depth is constant.

The inclination of the blood vessels is the change rate of the depth of a blood vessel, and is calculated using the length of the blood vessel and the depth of the blood vessel. That is, the inclination of the blood vessels is obtained by "Inclination of blood vessel=Depth of blood vessel/Length of blood vessel". In addition, a blood vessel may be divided into a plurality of sections, and the inclination of the blood vessel may be calculated in each section.

The area of the blood vessels is the number of pixels extracted as a blood vessel, or a value proportional to the number of pixels of the pixels extracted as the blood vessel. The area of the blood vessels is calculated regarding the inside of the area of interest, the outside of the area of interest, or the overall endoscopic image.

The density of the blood vessels is the percentage of blood vessels in a unit area. A region (for example, a region of a unit area) of a specific size including a pixel, from which the density of blood vessels is calculated, approximately at the center thereof is cut out, and the percentage of blood vessels occupied with respect to all the pixels within this region is calculated. By performing this on all the pixels of the area of interest or the overall endoscopic image, the density of the blood vessels of each pixel can be calculated.

The contrast of the blood vessels is the contrast of the observation object with respect the mucous membrane. The contrast of the blood vessels is calculated by "$Y_V/Y_M$" or "$(Y_V-Y_M)/(Y_V+Y_M)$", using the luminance $Y_V$ of blood vessels, and the luminance $Y_M$ of the mucous membrane.

The color of the blood vessels is respective values of RGB of pixels representing blood vessels. The change in the color of the blood vessels is a difference or a ratio between respective maximum and minimum values of respective RGB values of pixels representing blood vessels. For example, the ratio of a maximum value and a minimum value of B values of the pixels representing the blood vessels, the ratio of a maximum value and a minimum value of G values, or the ratio of a maximum value and a minimum value of R values represents the change in the color of the blood vessels. Of course, the color of the blood vessels and the change in the color of the blood vessels may be calculated regarding respective values of cyan, magenta, yellow, green, and the like through conversion into complementary colors.

The degree of meandering of the blood vessels is blood vessel information representing the breadth of a range where blood vessels meander and travel. The degree of meandering of the blood vessels is, for example, a minimum oblong area (number of pixels) including blood vessels from which the degree of meandering is calculated. Additionally, the ratio of the length of a blood vessel to a linear distance between a starting point and an end point of the blood vessel may be used as the degree of meandering of the blood vessels.

The blood density of the blood vessels is blood vessel information proportional to the amount of hemoglobin that a blood vessel includes. Since the ratio (G/R) of the G values to the R values in the pixels representing the blood vessels is proportional to the amount of hemoglobin, the blood concentration can be calculated for each pixel by calculating the value of G/R.

The degree of oxygen saturation of the blood vessels is the amount of oxyhemoglobin to the total amount of hemoglobin (the total amount of oxyhemoglobin and deoxyhemoglobin). The degree of oxygen saturation can be calculated using an endoscopic image obtained by imaging the observation object with light (for example, blue light with a wavelength of about 470±10 nm) of a specific wavelength band where a difference between the absorbance indexes of the oxyhemoglobin and the deoxyhemoglobin is large. Since the B values of the pixels representing the blood vessels has a correlation with the degree of oxygen saturation in a case where the blue light with a wavelength of about 470±10 nm is used, the degree of oxygen saturation of the respective pixels representing the blood vessels can be calculated by using a table or the like in which the B values are correlated with the degree of oxygen saturation.

The percentage of the arteries is the percentage of the number of pixels of arteries to the number of pixels of all blood vessels. Similarly, the percentage of the veins is the percentage of the number of pixels of veins to the number of pixels of all blood vessels. The arteries and the veins can be distinguished from each other by the degree of oxygen saturation. For example, assuming that blood vessels with the degree of oxygen saturation of 70% or more are the arteries, and blood vessels with the degree of oxygen saturation of less than 70% are the veins, extracted blood vessels are divided into the arteries and the veins. Thus, the percentage of the above arteries and the percentage of the veins can be calculated.

The concentration of the administered pigment is the concentration of the pigment sprayed onto the observation object, or the pigment injected into a blood vessel by intravenous injection. The concentration of the administered pigment is calculated, for example, in the percentage of the pixel value of a pigment color to the pixel value of pixels other than a pigment color. For example, in a case where a pigment colored in blue is administered, B/G, B/R, or the like represents the concentration of the pigment fixed (or temporarily adhered) to observation object.

The traveling pattern of the blood vessels is blood vessel information on the traveling direction of blood vessels. The traveling pattern of the blood vessels is, for example, the average angle (traveling direction) of blood vessels to an arbitrarily set reference, the dispersion (variations in traveling direction) of angles that the blood vessels makes with respect to the arbitrarily set reference line, or the like.

The blood flow rate (also referred to blood flow velocity) of the blood vessels is the number of red cells which pass through a blood vessel per unit time. For example, in a case where an ultrasonic probe is used together via a forceps channel or the like of the endoscope 12, the blood flow rate of the blood vessels from which the Doppler shift frequency of the respective pixels representing the blood vessels of the endoscopic image is calculated using a signal obtained by the ultrasonic probe can be obtained.

In a case where a portion of the endoscopic image is specified as the area of interest by the operation of the input device 87, the blood vessel information calculation unit 83 calculates the blood vessel information within the specified area of interest. In a case where the area of interest is not specified or in a case where the overall endoscopic image is specified as the area of interest, the blood vessel information calculation unit 83 calculates the blood vessel information in the overall endoscopic image. Additionally, some blood vessel information out of the above blood vessel information, such as the thickness, length, height difference, inclination, depth with the mucous membrane as a reference, and spacing of the blood vessels changes depending with positions within the endoscopic image. For this reason, in a case where blood vessel information with different values depending on positions within the endoscopic image are calculated, the blood vessel information calculation unit 83 uses the amounts of statistics, such as a maximum value, a minimum value, an average value, or a median value, as values of the blood vessel information. For example, assuming that the amount of statistics of a predetermined range (for example, a range of 99×99 pixels centered on an arbitrary pixel) is used as values of blood vessel information in an arbitrary pixel, blood vessel information that is hard to be calculated for each pixel can also be obtained for each pixel.

The blood vessel parameter calculation unit 84 calculates the blood vessel parameters by calculating using the plurality of items of blood vessel information calculated by the blood vessel information calculation unit 83. In the present embodiment, the blood vessel parameter calculation unit 84 calculates each blood vessel parameter by multiplying each of the plurality of items of blood vessel information calculated by the blood vessel information calculation unit 83 by a weighting coefficient and taking a sum. The weighting coefficient of each kind of blood vessel information is stored in a weighting coefficient table 91. The weighting coefficients stored in the weighting coefficient table 91 is determined in advance, for example, by machine learning.

In addition, in the present embodiment, weighting sums of the plurality of items of blood vessel information are calculated as the blood vessel parameters as described above. However, methods for calculating the blood vessel parameters are arbitrary. For example, the blood vessel parameters may be calculated not only by taking the sums but also by performing calculation in which addition, subtraction, multiplication, and division are present in a mixed manner, or the blood vessel parameters may be calculated using other functions.

Since the blood vessel parameters are calculated, for example, by adding blood vessel information with mutually different dimensions (units), there is no physical meaning in the blood vessel parameters, but these blood vessel parameters function as indexes of diagnosis. That is, the blood vessel parameters are different from the blood vessel information that these parameters are values without physical meanings.

Figure 4:
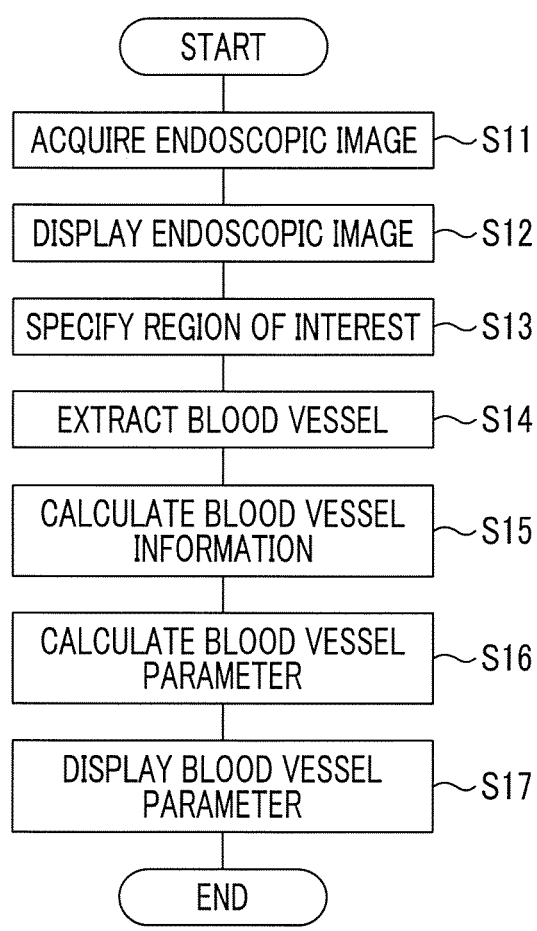
FIG. 4 is a flowchart illustrating the operation of the image processor.
Figure 5:
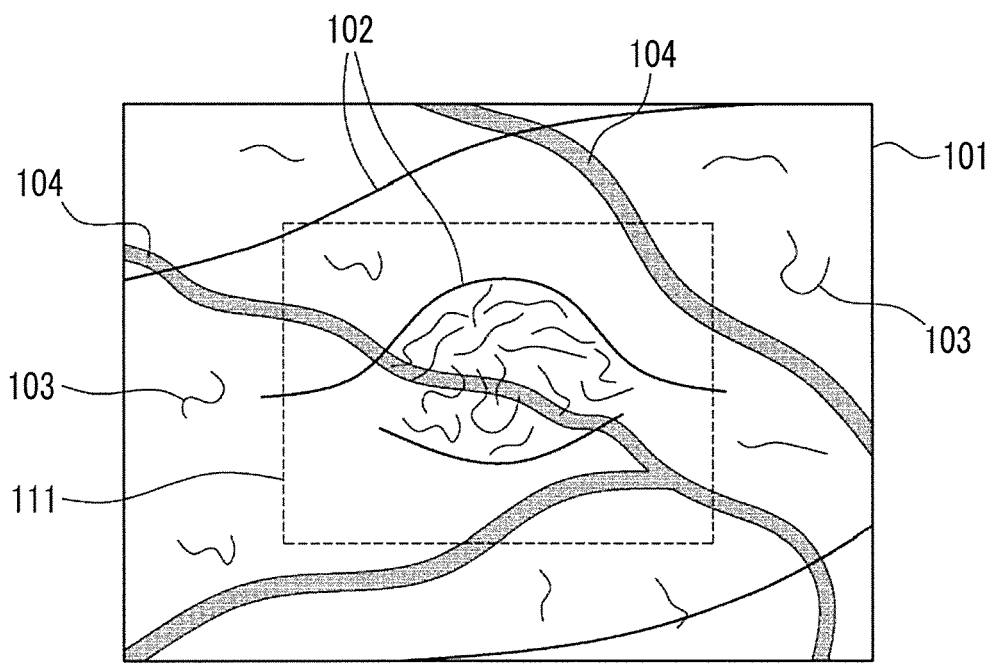
FIG. 5 is an explanatory view of a special observation image.

Next, a flow of the operation of the image processor 65 will be described along a flowchart of FIG. 4. First, the image processor 65 acquires an endoscopic image from the storage 64 using the image acquisition unit 81 according to the input operation of the input device 87 (S11), and displays the acquired endoscopic image on the monitor 88 (S12). In the present embodiment, since the image acquisition unit 81 acquires a special observation image in which blood vessels are enhanced in colors from the storage 64, as illustrated in FIG. 5, a special observation image 101 is displayed on the monitor 88. The special observation image 101 is the endoscopic image which the blood vessels enhanced in colors. For example, a shape 102 of a front surface that is a mucous membrane of an observation object can be observed. In addition, a thin surface layer blood vessel 103 at a position relatively near the surface of the mucous membrane is expressed in a magenta-based color, and a thick middle-depth blood vessel 104 at a relatively deep position under the mucous membrane is enhanced by being expressed in a cyan-based color.

As the special observation image 101 is displayed on the monitor 88 as described above, the area-of-interest 111 is specified as the need arises (S13). For example, in the case of the special observation image 101 of FIG. 5, a place with the possibility of a lesion is present near the center of the image. Thus, the vicinity of the center of the special observation image 101 including the place with the possibility of this lesion is specified as the area-of-interest 111.

Figure 6:
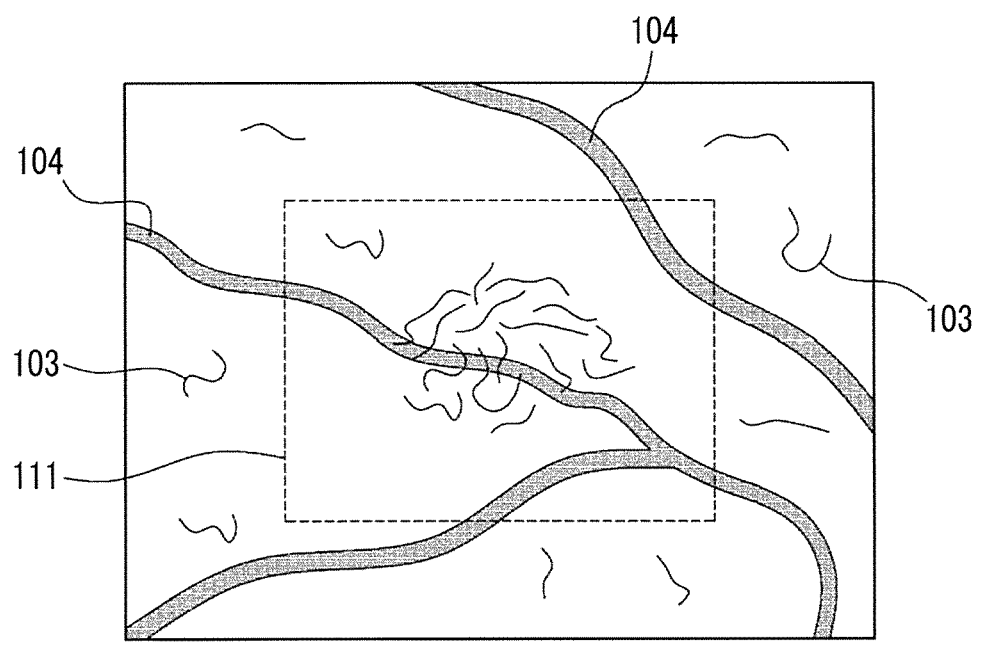
FIG. 6 is an explanatory view illustrating blood vessels extracted from the special observation image.

On the other hand, the blood vessel extraction unit 82 extracts the blood vessels of the observation object from the special observation image 101 acquired by the image acquisition unit 81 (S14). In the case of the special observation image 101, as illustrated in FIG. 6, the blood vessel extraction unit 82 extracts the surface layer blood vessel 103 and the middle-depth-layer blood vessel 104.

As the blood vessel extraction unit 82 extracts the blood vessels, the blood vessel information calculation unit 83 calculates a plurality of items of blood vessel information using the extracted blood vessels of the blood vessels by the blood vessel extraction unit 82 (S15). As described above, since the surface layer blood vessel 103 and the middle-depth-layer blood vessel 104 are extracted from the special observation image 101, the blood vessel information calculation unit 83 calculates the number, thickness, length, height difference, inclination, area, density, depth with the mucous membrane as a reference, and spacing of the surface layer blood vessel 103 and the middle-depth-layer blood vessel 104, within the specified area-of-interest 111.

Figure 7:
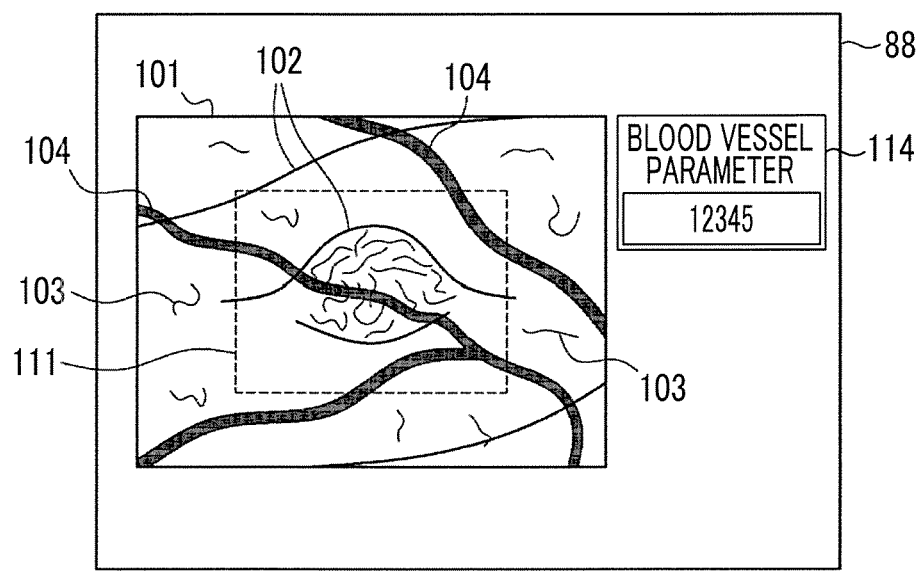
FIG. 7 is an explanatory view illustrating a monitor that displays blood vessel parameters.

Thereafter, the blood vessel parameter calculation unit 84 calculates blood vessel parameters by performing calculating using the above respective items of blood vessel information calculated by the blood vessel information calculation unit 83 and the weighting coefficients stored in the weighting coefficient table 91 (S16). The calculated blood vessel parameters are transmitted to the monitor 88, and as illustrated in FIG. 7, are displayed on a blood vessel parameter display unit 114 set on the monitor 88, together with the special observation image 101.

As described above, the image processor 65 selects the endoscopic image (special observation image 101) from the storage 64, and displays the selected endoscopic image on the monitor 88. As the area-of-interest 111 is specified, the surface layer blood vessel 103 within the specified area-of-interest 111 and the blood vessel parameters regarding the middle-depth-layer blood vessel 104 are displayed together with the special observation image 101. Then, since the blood vessel parameters are numerical values calculated using the plurality of items of blood vessel information in imitation of doctors performing diagnosis from multifaceted and complex points of sight, the doctor can determine the state of then observation object quickly and accurately assuming that the numerical values of the blood vessel parameters are seen. That is, the image processor 65 can support diagnosis by calculating the blood vessel parameters calculated by the calculation using the plurality of items of blood vessel information. For example, as compared to a case where the plurality of items of blood vessel information to be used for the calculation of the blood vessel parameters are presented to the doctor, respectively, the image processor 65 can present more direct information to diagnostic contents called the blood vessel parameters to support diagnosis.

Figure 8:
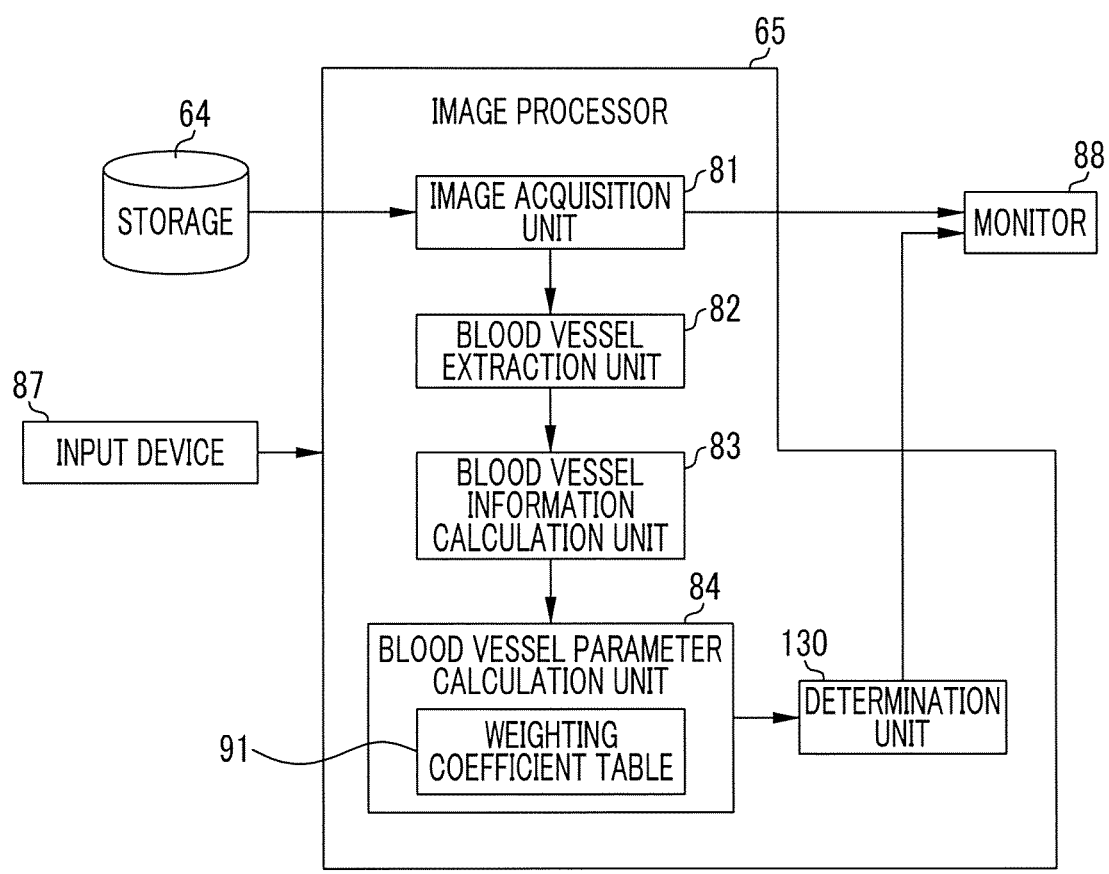
FIG. 8 is a block diagram of the image processor having a determination unit.

Although the blood vessel parameters are displayed on the monitor 88 in the above embodiment, as illustrated in FIG. 8, it is preferable to provide the image processor 65 with the determination unit 130 that determines the state of the mucous membrane of the observation object using the blood vessel parameters, and to display determination results obtained by the determination unit 130 instead of the blood vessel parameters on the monitor 88.

Figure 9:
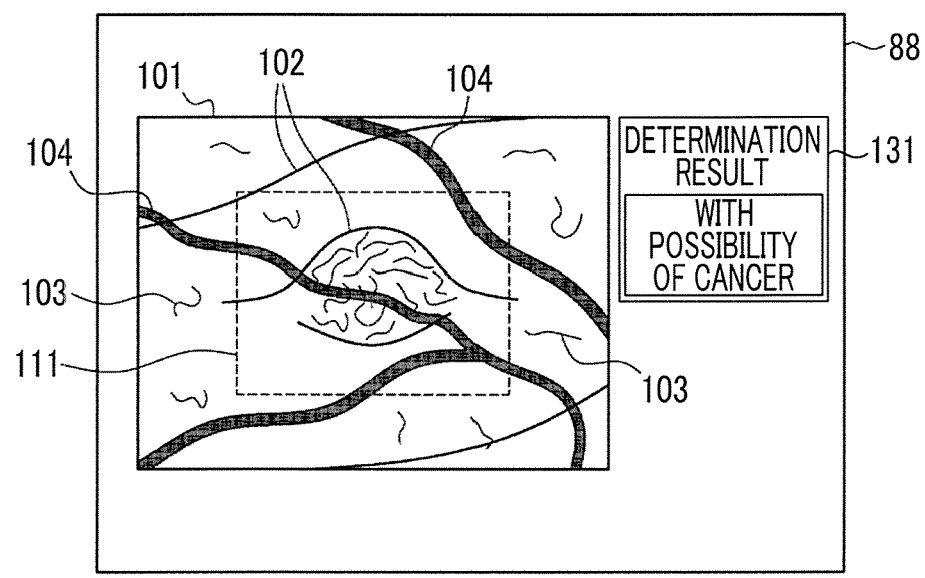
FIG. 9 is an explanatory view illustrating the monitor that displays a determination result of the state of a mucous membrane.

The determination unit 130 acquires the blood vessel parameters from the blood vessel parameter calculation unit 84, and determines the state of the mucous membrane of the observation object on the basis of the values of the blood vessel parameters or by performing further calculation using the blood vessel parameters. For example, in a case where the weighting coefficients to be used for the calculation of the blood vessel parameters are adjusted in order to determine the state of the mucous membrane as three kinds of states including normality, adenoma, and cancer, the determination unit 130 determines that the mucous membrane of the observation object is normal in a case where the blood vessel parameters are equal to or smaller than a first threshold value, and determines that there is a suspicion of adenoma in a case where the blood vessel parameters are greater than the first threshold value and equal to and smaller than a second threshold value. In a case where the blood vessel parameters are greater than the second threshold value, it is determined there is a possibility of progressing to cancer. The determination unit 130 displays the determination results together with the special observation image 101 on a determination result display unit 131 set on the monitor 88 as is illustrated in FIG. 9, by transmitting the determination results regarding the state of the mucous membrane to the monitor 88.

As described above, as the determination unit 130 is provided in the image processor 65 to determine the state of the mucous membrane of the observation object using the blood vessel parameters, and displays the results, diagnosis can be supported more directly than that in a case where the blood vessel parameters are displayed.

In addition, it is desirable that the determination unit 130 determines the state of the mucous membrane as three or more kinds of states including normality, adenoma, and cancer, as in the above modification example. Particularly, in a case where the state of a mucous membrane of the large intestine is determined, it is desirable to determine the state of the mucous membrane as any one of states including normality, hyperplastic polyp (HP), sessile serrated adenoma polyp (SSA/P), traditional serrated adenoma (TSA), laterally spreading tumor (LST), and cancer. In a case where the determination results of the determination unit 130 are subdivided in this way, it is preferable that the determination unit 130 uses the blood vessel information in addition to the blood vessel parameters. In the related art, it was considered that the hyperplastic polyp had a low risk of canceration and had no necessity for treatment. However, in recent years, since an example in which the SSA/P similar to the hyperplastic polyp was cancerated is also discovered, it is becoming important to differentiate particularly between the hyperplastic polyp and the SSA/P. Meanwhile, assuming that a middle-depth-layer blood vessel is crossing the bottom of a thickened mucous membrane believed to be the hyperplastic polyp or SSA/P, it is known that the SSA/P is highly likely to form. Assuming that the blood vessel parameters are used, the hyperplastic polyp and the SSA/P can be differentiated by the determination unit 130. However, assuming that determination is performed by combining the blood vessel parameters and the blood vessel information (the thickness and length of the blood vessels), the SSA/P can be differentiated from the hyperplastic polyp with higher probability.

Additionally, in a case where the state of the mucous membrane of the observation object is cancer, it is preferable that the determination unit 130 further determines the stage of the cancer using the blood vessel parameters. It is preferable to display the stage of the cancer determined by the determination unit 130 on the determination result display unit 131. In this way, as the stage is further determined and the result is displayed on the monitor 88 in a case where the state of the mucous membrane of the observation object is determined to be cancer, diagnosis can be supported more finely.

Figure 10:
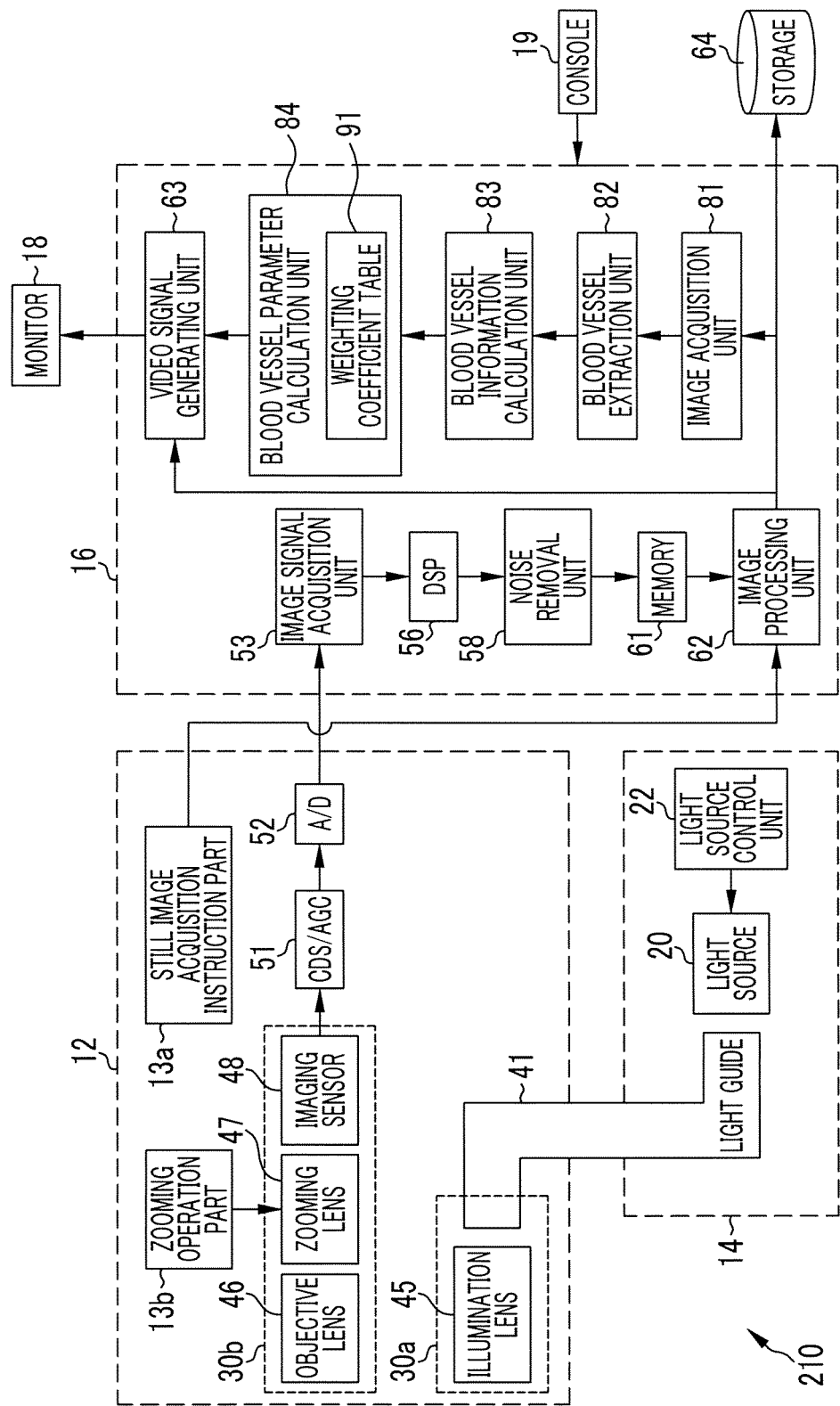
FIG. 10 is a block diagram of the endoscope system that calculates the blood vessel parameters using a processor device.

In the above embodiment, the endoscope system 10 saves the endoscopic image in the storage 64, and then, the image processor 65 calculates the blood vessel parameters by acquiring the endoscopic image from the storage 64. However, the blood vessel parameters may be calculated substantially in real time, observing the observation object. In this case, as in an endoscope system 210 illustrated in FIG. 10, the processor device 16 is provided with the image acquisition unit 81, the blood vessel extraction unit 82, the blood vessel information calculation unit 83, and the blood vessel parameter calculation unit 84. The configurations of the endoscope 12 and the light source device 14 are the same as those of the endoscope system 10 of the first embodiment.

In a case where the processor device 16 is provided with the respective units of the image processor 65 in this way, the image acquisition unit 81 directly acquires the endoscopic image generated by the signal processing unit 62 from the signal processing unit 62 without the interposition of the storage 64. The functions that the blood vessel extraction unit 82 extracts the blood vessels from the endoscopic image acquired by the image acquisition unit 81 and calculates the plurality of items of blood vessel information on the blood vessels extracted by the blood vessel information calculation unit 83, and the blood vessel parameter calculation unit 84 performs calculation using the plurality of items of calculated blood vessel information and the weighting coefficients stored in the weighting coefficient table 91 and the calculation of the blood vessel parameters are the same as that of the image processor 65. In a case where the area-of-interest 111 is specified, the console 19 or buttons (not illustrated) provided in the operating part 12b of the endoscope 12 are used instead of the input device 87. The blood vessel parameter calculation unit 84 displays the blood vessel parameters together with the endoscopic image capable of being controlled by the signal processing unit 62 on the monitor 18 by transmitting the calculated blood vessel parameters to the video signal generating unit 63.

As described above, as the processor device 16 is provided with the image acquisition unit 81, the blood vessel extraction unit 82, the blood vessel information calculation unit 83, and the blood vessel parameter calculation unit 84 that constitute the image processor 65, the processor device 16 functions as the image processor 65. For this reason, in the endoscope system 210, the blood vessel parameters are calculated and displayed, observing the observation object. Therefore, diagnosis can be supported in real time.

In addition, it is preferable that the endoscope system 210 calculates and displays the blood vessel parameter in a case where the signal processing unit 62 receives a still image acquisition instruction from at least the still image acquisition instruction part 13a. Of course, in a case where a moving picture of the endoscopic image is displayed on the monitor 18 regardless of the presence/absence of the input of the still image acquisition instruction, the blood vessel parameters may be calculated and displayed. In a case where the moving picture of the endoscopic image is displayed on the monitor 18, the blood vessel parameters may be calculated and displayed regarding the endoscopic image of all frames of the moving picture. However, even assuming that the blood vessel parameters are calculated and displayed at every several frames, the blood vessel parameters can be substantially calculated and displayed in real time.

Figure 11:
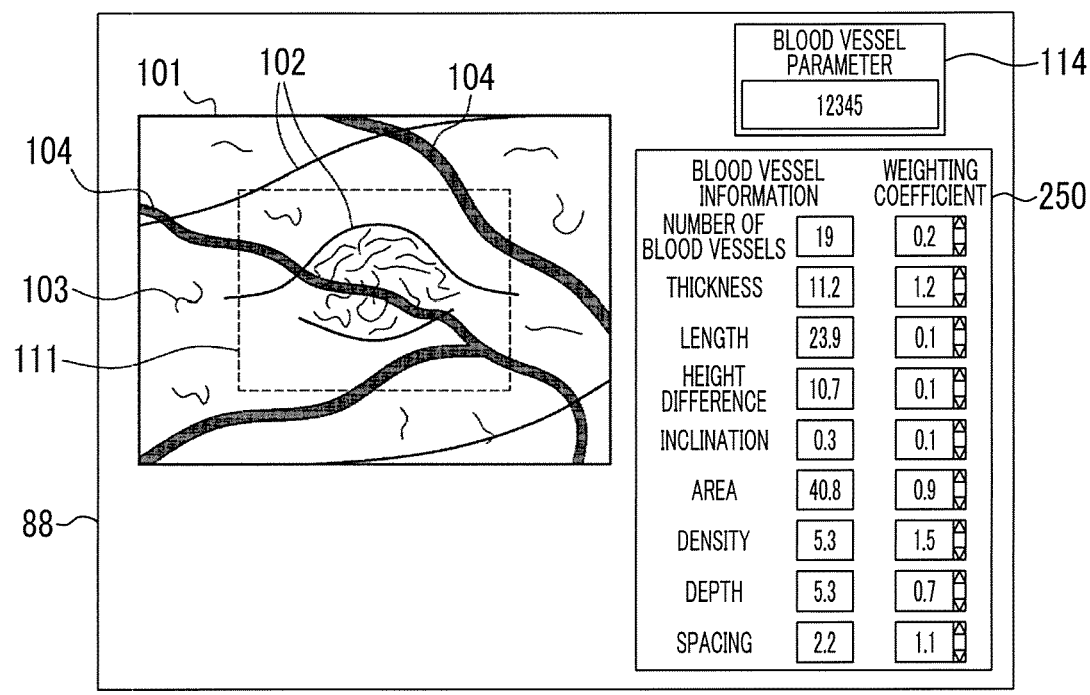
FIG. 11 is an explanatory view illustrating the monitor that displays blood vessel information and weighting coefficients.

In the above embodiment, the blood vessel parameters are displayed on the monitor 88 of the image processor 65. In addition, it is preferable to display the blood vessel information and the weighting coefficients to be used in order that the blood vessel parameters are calculated. For example, as illustrated in FIG. 11, in the case of the image processor 65, an information display unit 250 is displayed in addition to the blood vessel parameter display unit 114. The blood vessel information calculated by the blood vessel information calculation unit 83 and the weighting coefficients read from the weighting coefficient table 91 are associated with each other and displayed on the information display unit 250. The same applies to the case of the endoscope system 210, and in addition to the determination results obtained by the determination unit 130, the blood vessel parameters, and the blood vessel information and the weighting coefficients to be used for the calculation of the blood vessel parameters are displayed on the monitor 18. In FIG. 11, although both the blood vessel information and the weighting coefficients are displayed, only the blood vessel information or only the weighting coefficients may be displayed in addition to the blood vessel parameters and the determination results. In this way, it becomes easy for doctors to ascertain the meaning of the blood vessel parameters and the ground for the determination by displaying the blood vessel information and the weighting coefficients to be used for the calculation of the blood vessel parameters.

Additionally, for example, in a case where a "confirmation mode" in which the blood vessel information and the weighting coefficients are additionally displayed is provided, and setting to the confirmation mode is performed using the input device 87 or the like (the operating part 12b, the console 19, a foot pedal (not illustrated), or the like in the case of the endoscope system 210), the blood vessel information and the weighting coefficients may be displayed in addition to the blood vessel parameters and the determination results.

Additionally, as described above, in a case where the weighting coefficients are displayed in addition to the blood vessel parameters and the determination results, it is preferable that the weighting coefficients are made to be changeable using the input device 87, the console 19, or the like. In a case where the weighting coefficients are changed, the blood vessel parameter calculation unit 84 re-calculates blood vessel parameters using weighting coefficients after change, and the determination unit 130 performs re-determination using blood vessel parameters calculated using the weighting coefficients after change. In this way, as the weighting coefficients are displayed and the weighting coefficients are made to be changeable, methods for adjusting the methods for calculating and determining the blood vessel parameters on the basis of doctors' experience can be provided.

Figure 12:
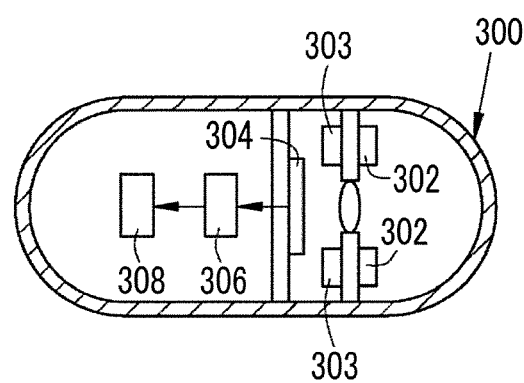
FIG. 12 is a schematic view of a capsule endoscope.

In the above embodiment, the invention is carried out by the endoscope system 10 that performed observation by inserting the endoscope 12 provided with the imaging sensor 48 into a subject. However, a capsule endoscope system is also suitable for the invention. For example, as illustrated in FIG. 12, the capsule endoscope system has at least a capsule endoscope 300 and a processor device (not illustrated). The capsule endoscope 300 includes a light source 302, a light source control unit 303, an imaging sensor 304, an image signal acquisition processing unit 306, and a transmitting and receiving antenna 308. The light source 302 is configured similar to the light source 20 of the endoscope system 10, and emits illumination light through the control of the light source control unit 303. The image signal acquisition processing unit 306 functions as the image signal acquisition unit 53, the DSP 56, the noise removal unit 58, and the signal processing unit 62. The processor device of the capsule endoscope system is configured similar to the processor device 16 of the endoscope system 210, and also functions as the image processor 65. The endoscopic image generated by the image signal acquisition processing unit 306 is transmitted to the processor device via the transmitting and receiving antenna 308. In a case where the blood vessel parameters are calculated in real time by the capsule endoscope 300, the image signal acquisition processing unit 306 may be made to further function also as the image acquisition unit 81, the blood vessel extraction unit 82, the blood vessel information calculation unit 83, and the blood vessel parameter calculation unit 84.

What is claimed is:

1. An image processor comprising:
a processor; and
a memory electrically connected to the processor, wherein the processor is configured to:
  acquire an endoscopic image captured by an endoscope;
  extract an image of blood vessels from an observation object projected on the endoscopic image, using a specific area of the endoscopic image;
  calculate a plurality of items of blood vessel information from the image of blood vessels, wherein the plurality of items of the blood vessel information includes at least two or more among the number of pieces, the number of branches, a branch angle, a distance between branch points, the number of intersections, thickness, a change in thickness, the degree of complexity of a change in thickness, length, intervals, depth with a mucous membrane as a reference, a height difference, inclination, area, density, contrast, color, a change in color, the degree of meandering, blood concentration, the degree of oxygen saturation, the percentage of arteries, the percentage of veins, the concentration of an administered pigment, a traveling pattern, and a blood flow rate, in terms of the blood vessels;
  calculate a blood vessel parameter which is a value without physical meaning and functions as an index of diagnosis by adding the plurality of items of blood vessel information with mutually different dimensions within the specified area of the endoscope image; and
  determine a state of the mucous membrane of the observation object, using the blood vessel parameter.

2. The image processor according to claim 1,
wherein the blood vessel information is values of the blood vessel information in a whole or partial region of the endoscopic image.

3. The image processor according to claim 2,
wherein the blood vessel information is a maximum value, a minimum value, an average value, or a median value in the whole or partial region of the endoscopic image.

4. The image processor according to claim 1,
wherein the processor performs calculating the blood vessel parameter by performing weighting on the plurality of items of blood vessel information, and calculates the blood vessel parameter.

5. The image processor according to claim 4,
wherein the processor performs the weighting, using predetermined coefficients through machine learning.

6. The image processor according to claim 1,
wherein the processor determines the state of the mucous membrane of the observation object as any one of three or more kinds of states including normality, adenoma, and cancer, using the blood vessel parameter.

7. The image processor according to claim 1,
wherein the processor determines the state of the mucous membrane of the observation object as any one of states including normality, hyperplastic polyp, SSA/P, adenoma, laterally spreading tumor, and cancer, using the blood vessel parameter.

8. The image processor according to claim 1,
wherein the processor is further configured to determine the stage of cancer, using the blood vessel parameter, in a case where the state of the mucous membrane of the observation object is cancer.

9. An endoscope system comprising:
an endoscope that images an observation object; and
a processor device configured to acquire an endoscopic image captured by the endoscope, to extract an image of blood vessels of the observation object projected on the endoscopic image, using a specific area of the endoscopic image, to calculate a plurality of items of blood vessel information from the image of blood vessels, wherein the plurality of items of the blood vessel information includes at least two or more among the number of pieces, the number of branches, a branch angle, a distance between branch points, the number of intersections, thickness, a change in thickness, the degree of complexity of a change in thickness, length, intervals, depth with a mucous membrane as a reference, a height difference, inclination, area, density, contrast, color, a change in color, the degree of meandering, blood concentration, the degree of oxygen saturation, the percentage of arteries, the percentage of veins, the concentration of an administered pigment, a traveling pattern, and a blood flow rate, in terms of the blood vessels, to calculate a blood vessel parameter which is a value without physical meaning and functions as an index of diagnosis by adding the plurality of items of blood vessel information with mutually different dimensions within the specified area of the endoscope image, and to determine a state of the mucous membrane of the observation object, using the blood vessel parameter.

10. An image processing method comprising:
a step in which a processor acquires an endoscopic image captured by an endoscope;
a step in which the processor extracts an image of blood vessels from an observation object projected on the endoscopic image, using a specific area of the endoscopic image;
a step in which the processor calculates a plurality of items of blood vessel information from the image of blood vessels, wherein the plurality of items of the blood vessel information includes at least two or more among the number of pieces, the number of branches, a branch angle, a distance between branch points, the number of intersections, thickness, a change in thickness, the degree of complexity of a change in thickness, length, intervals, depth with a mucous membrane as a reference, a height difference, inclination, area, density, contrast, color, a change in color, the degree of meandering, blood concentration, the degree of oxygen saturation, the percentage of arteries, the percentage of veins, the concentration of an administered pigment, a traveling pattern, and a blood flow rate, in terms of the blood vessels;

a step in which the processor calculates a blood vessel parameter which is a value without physical meaning and functions as an index of diagnosis by adding using the plurality of items of blood vessel information with mutually different dimensions within the specified area of the endoscope image; and a step in which the processor determines a state of the mucous membrane of the observation object, using the blood vessel parameter.

\* \* \* \* \*